United States Patent [19]

Wenteler et al.

[11] Patent Number: 5,008,471
[45] Date of Patent: Apr. 16, 1991

[54] PROCESS FOR THE PREPARATION OF ROOPEROL

[75] Inventors: George L. Wenteler, Pretoria; Karl H. Pegel, Durban; Siegfried Drews, Pietermaritzburg; Hans Kündig, Witpoort/Midrand, all of South Africa

[73] Assignee: Rooperol (N.A.), Kralendikj, Netherlands

[21] Appl. No.: 365,751

[22] Filed: Jun. 13, 1989

Related U.S. Application Data

[63] Continuation-in-part of Ser. No. 875,398, Jun. 17, 1986, abandoned.

[30] Foreign Application Priority Data

Jun. 19, 1985 [ZA] South Africa ............ 84/4640

[51] Int. Cl.$^5$ ............ C07C 39/215; C07C 37/11
[52] U.S. Cl. ............ 568/729; 568/763
[58] Field of Search ............ 568/729, 715, 717, 763, 568/766

[56] References Cited

U.S. PATENT DOCUMENTS 4,644,085  2/1987  Drewes et al. ............ 558/729

FOREIGN PATENT DOCUMENTS 0130829  1/1985  European Pat. Off. ............ 568/729
0206765  12/1986  European Pat. Off. ............ 568/729
2120650  12/1983  United Kingdom ............ 568/729

OTHER PUBLICATIONS

Gaylord "Reduction with Complex Metal Hydrides" pp. 1007–1024 Interscience Pub., Inc. NY (1956).

Primary Examiner—Werren B. Lone
Attorney, Agent, or Firm—Vidas & Arrett

[57] ABSTRACT

As a process for preparing a compound of the formula

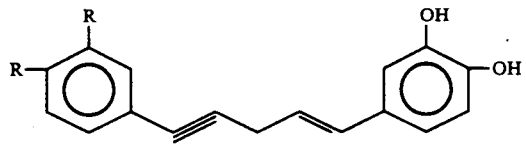

in which both Rs are H or —OH comprising the steps:

a. of treating the ethyl ester of caffeic acid with a trialkylsilyl chloride at ambient conditions in equimolar proportions in the presence of a base;
b. of reduction of the resulting product with an aluminium hydride reagent at sub-zero temperature and equimolar proportions to yield the corresponding allylic alcohol;
c. of halogenation of this allylic alcohol with thionyl chloride or a phosphorus trihalide to yield the corresponding allyl halide;
d. of coupling this allyl halide with the silyl ether of compound of the formula

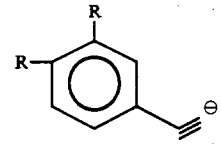

in refluxing ether solutions; and
e. of hydrolysis of this coupled product with tetra alkyl ammonium flouride at ambient conditions and of equimolar proportions.

1 Claim, No Drawings

PROCESS FOR THE PREPARATION OF ROOPEROL

REFERENCE TO RELATED CASES

This application is a continuation-in-part of Ser. No. 875,398 filed June 17, 1986, now abandoned, the disclosure of which is incorporated herein by reference. The application is also related to an application for same inventors entitled PROCESS FOR THE PREPARATION OF ROOPEROL DERIVATIVE filed concurrently herewith as a continuation-in-part of Ser. No. 875,398.

FIELD OF THE INVENTION

The invention relates to the preparation of the compound Rooperol.

BACKGROUND OF THE INVENTION

The isolation of E-1,5-bis(3,4-dihydroxyphenyl)pent-4-en-1-yne 4,4 di-$\beta$-D-glucopyranoside, Hypoxoside, from *Hypoxis obtusa* and *Hypoxis rooperi* has been described by Marini-Bettolo[1] and Drewes[2]. The use of Hypoxoside, Rooperol and related pent-4-en-1-yne derivatives in anticancer compositions are disclosed (U.S. Pat. No. 4 644 085, European Patent No. 130829). The preparation of Rooperol by the hydrolysis of Hypoxoside in water at a pH 6.3 with B-glucosidase at preferably 37° C., the preparation of the tetra-acetate from Rooperol by acylation with ($Ac_2O/C_5H_5N$), and also the preparation of tetramethoxy-rooperol from Rooperol by methylation with diazomethane has been disclosed [1,2]. The synthesis of the tetramethoxy derivative of Rooperol is achieved by the conversion of 3,4-dimethoxybenzaldehyde to the alkynide anion of 3,4-dimethoxyethynylbenzene (3 steps) and subsequent coupling to 3,4-dimethoxycinnamyl chloride obtained from 3-(3,4-dimethoxyphenyl)prop-2-enoic acid (3 steps) via copper catalysis. Similar synthetic sequences using phenyl rings with no substituents or precursors in which one or both phenyl rings carry methoxy- or methylenedioxy substituents, have been described.[2] Although a variety of protecting groups have been used, the removal of these protecting groups to yield Rooperol has been unsuccessful due to the highly reactive nature of the pent-4-en-1-yne system. It is the object of this invention to provide a process for the synthesis of Rooperol, and its phenolic analogues.

SUMMARY OF THE INVENTION

According to the invention a process for preparing a compound of the formula

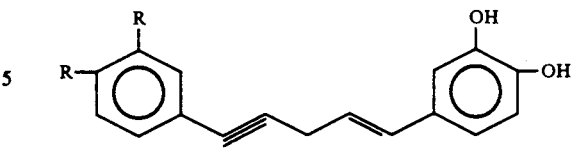

in which both Rs are H or —OH comprising the steps:

a. of treating the ethyl ester of caffeic acid with a t-butyldimethylsilyl chloride at ambient conditions in a 1.2 molar proportion in the presence of a base;

b. of reduction of the resulting product with an excess aluminium hydride reagent at sub-zero temperature and at least equimolar proportions to yield the corresponding allylic alcohol;

c. of halogenation of this allylic alcohol with thionyl chloride or a phosphorus trihalide to yield the corresponding allyl halide;

d. of coupling this allyl halide with the silyl ether of compound of the formula

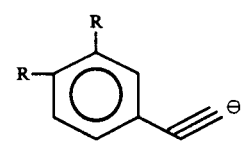

(R = H or OH)

in refluxing ether solutions; and e. of hydrolysis of this coupled product with tetra alkyl ammonium fluoride at ambient conditions and of equimolar proportions.

In a preferred form of the invention the phenolic hydroxy groups in caffeic acid ester are protected by their conversion to silyl ethers by using t-butyldimethylsilyl chloride and a base such as imidazole. The silyloxy ester is reduced to the corresponding alcohol with an excess of DIABAH or $LiAlH_4$.

The conversion of the alcohol to the corresponding halide proceeds smoothly by standard methods. The silyl ether of 3,4-dihydroxyphenylacetylene is prepared by:

(i) treating 3,4-dihydroxybenzaldehyde with t-butyldimethylsilyl chloride and imidazole as a base;

(ii) conversion of the carbonyl group to the corresponding 2,2-vinyl dibromide by the method of E. J. Corey[3] followed by dehydrohalogenation with two equivalents of butyl lithium.

(iii) alkylation of 3-(3',4'-t-butyldimethylsiloxy phenyl)-1- haloprop-2-ene with the formed anion in (ii) and (iv) the deprotection of the silyl ether groups is achieved with a tetraalkylammonium fluoride e.g. tetraethylammonium fluoride to yield rooperol.

The reactions are outlined in the following scheme.

Scheme

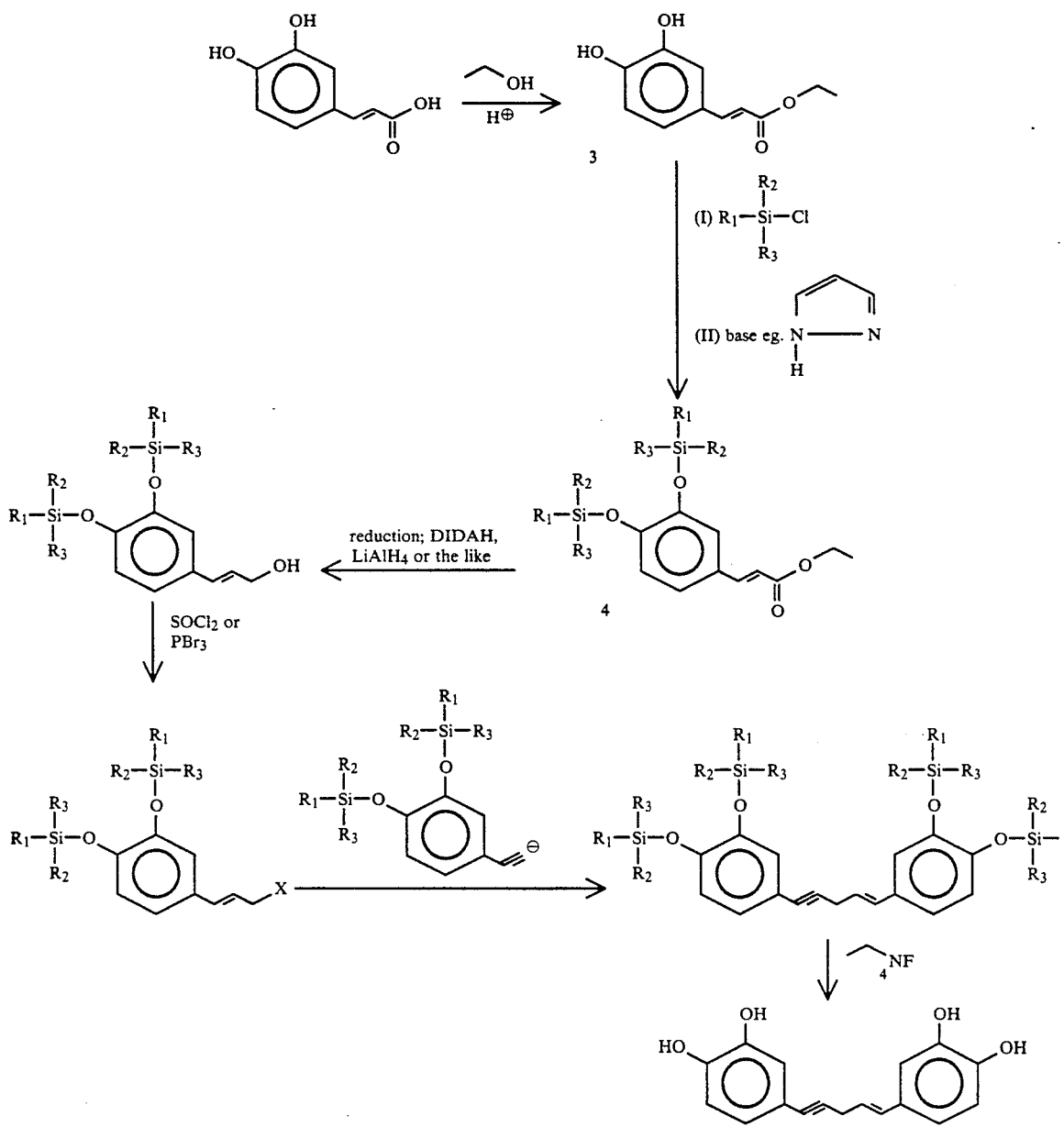

Where:

X = Halogen (I, Br)

$R_1 = R_2 = CH_3$

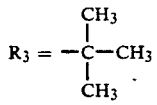

PROCEDURES

I. Synthesis of the ethyl ester of caffeic acid

Method

A solution of caffeic acid (10.0 g, 0.055 mol) in a mixture of benzene (300 ml), ethanol (80 ml) and H₂SO₄(conc. 5 ml) is refluxed for 34 hours. The cooled dark green reaction mixture is neutralized with a saturated aqueous NaHCO₃ solution. The aqueous layer is then extracted with ether (3×15 ml), dried (MgSO₄) and the combined organic extracts concentrated to yield a brown crystalline product (9.0 g, 78%). Recrystallization from ethyl acetate yielded the ethyl ester of caffeic acid as a light brown crystalline product (5.98 g, 52%) mp 143°-146° C.; δH(acetone; 80 MHz; TMS): 1.27(3 H, t, J=7.1 Hz,CH₂C$\underline{H}$₃); 4.2(2 H, t, J=7.1 Hz, CH$_2$CH$_3$), 6.27(1 H, d, J=15.9 Hz, H-2) 6.82–7.18(3 H, m, ArH), and 7.55(1 H, d, J=15.9 Hz, H-3).

II. Protection of the aromatic OH groups as t-butyldimethylsilyl ethers

A solution of the ethyl ester of caffeic acid (1 eqv), t-butyldimethylchlorosilane (1.1 eqv per OH group), and imidazole (1.2 eqv) in DMF is stirred for 24 hours at 23° C. The solution is quenched with a saturated aqueous solution of NaHCO$_3$ and extracted with ether. The combined extracts are washed with water, dried (MgSO$_4$), and the solvent evaporated to provide a crude product which is purified by suitable methods to yield the disilyl ether of the ethyl ester of caffeic acid (compound 4 in the Scheme).

Compound 4

$\delta$(CDCl$_3$; 80 MHz, TMS): 0.25(12 H, s, —Si—CH$_3$, 0.90(18 H, s, Si+CH$_3$), 1.33(3 H, t, J=7.08 Hz, CH$_2$CH$_3$), 4.25(2 H, q, J=7.08 Hz, CH$_2$—CH$_3$), 6.22(1 H, d, J=15.8 Hz, H-2); 6.75-7.06(3 H, m, ArH) and 7.57(1 H, d, J=15.8 Hz, H-3).

III. Synthesis of 3-[3,4-di(t-butyldimethylsiloxy)phenyl]prop-2-en-1-ol

Method

DIBAH (175 mg, 0.274 mmol) in toluene (3.3 ml) is added to a solution of the disilyl ether of the ester (4) (500 mg, 0.114 mmol) in toluene (1.5 ml) at −78° C. over a period of 1 hour. The reaction mixture is then allowed to reach room temperature when it is quenched with saturated aqueous NH$_4$Cl (10 ml) and extracted with ethyl acetate (3×10 ml). The combined extracts are dried (MgSO$_4$) and concentrated to provide a light yellow oil of 3-[3',4'-di(t-butyldimethylsiloxy)phenyl]-prop-2-en-1-ol (350 mg, 78%); $\delta_H$(CDCl$_3$; 80 MHz; TMS): 0.25(12 H, s, SiCH$_3$), 0.9(18 H, s, Si+CH$_3$), 1.22–1.28(2 H, m, CH$_2$), 4.22(1 H, d, J=5.1 Hz, H-2), 6.20(1 H, d, J=5.1 Hz, H-3) and 6.69–6.85(3 H, m ArH).

IV. Conversion to the corresponding allylic chloride compound

By standard laboratory techniques using SO$_2$Cl$_2$ or PCl$_3$.

V. Synthesis of 3,4-di(t-butyldimethylsiloxy)-2',2'-dibromostyrene

Method

A suspension of activated zinc (1.90 g, 0,029 mol, 2 eqv), triphenylphosphine (7.60 g, 0.0029 mol, 2 eqv) and carbon tetrabromide (9.60 g, 0.029 mol, 2 eqv) in dry CH$_2$Cl$_2$ (20 ml) is stirred for 30 hours under N$_2$. To this Wittig reagent is added 3,4-di(t-butyldimethylsiloxy) benzaldehyde (5.50 g, 0.015 mol) and the mixture is stirred for 3 hours at room temperature before it is quenched with pentane (50 ml) and filtered. The residue is washed with CH$_2$Cl$_2$ (30 ml) and the organic solvents are evaporated to provide the dibromide as a yellow oil (5.08 g, 66%). $\delta_H$(CDCl$_3$; 80 MHz, TMS): 0.25(12 H, s, —Si—CH$_3$), 0.90(18 H, s, Si+CH$_3$) and 6.82(1 H, s, CH) and 7.20–7.33(3 H, m, ArH).

VI. Synthesis of 3,4-di(t-butyldimethylsiloxy) phenylethyne

Method

To a solution of 3,4-di(t-butyldimethylsiloxy)-2,2-dibromostyrene (3.00 g, 0.006 mol) in dry tetrahydrofuran (10 ml) is added BuLi (2 eqv) at −78° C. over a period of 1 hour. The reaction mixture is allowed to reach room temperature when it is quenched with saturated aq. NaHCO$_3$ (20 ml), extracted with ehtyl acetate (3×20 ml) and the combined extracts are dried (MgSO$_4$) before the solvent was evaporated under reduced pressure to provide the corresponding acetylenic product as a dark brown oil (1.8 g, 86%). $\delta_H$(CDCl$_3$; 80 MHz, TMS): 0.25(12H, s, —Si—CH$_3$), 0.9(18 H, s, Si—CH$_3$), 2.96(1 H, s, CH), and 6.69–7.26(3 H, m, ArH).

VII. Preparation of 3',4'-di(t-butyldimethylsiloxy) phenylacetylide magnesium bromide Bromoethane (1 mol equiv) is added dropwise to a stirred mixture of magnesium metal (1.05 mol equiv) and tetrahydrofuran under anhydrous conditions and a N$_2$ atmosphere. Once the exothermic reaction has subsided, the reaction mixture is refluxed for 10 minutes, cooled to 20° C. and the alkyne as prepared in VI (1.05 mol equiv) dissolved in THF is added dropwise. Ethane is evolved during the formation of the corresponding phenylacetylide magnesium bromide. The mixture is then refluxed for 45 minutes and cooled to 20° C.

VIII. Preparation of phenylacetylide magnesium bromide

Bromoethane (1 mol equiv) is added dropwise to a stirred mixture magnesium metal (1.05 mol equiv) and tetrahydrofuran under anhydrous conditions and a N$_2$ atmosphere. Once the exothermic reaction has subsided, the reaction mixture is refluxed for 10 minutes, cooled to 20° C. and the alkyne (1.05 mol equiv) dissolved in THF is added dropwise. Ethane is evolved during the formation of the phenylacetylide magnesium bromide. The mixture is then refluxed for 45 minutes and cooled to 20° C.

IX. Reaction with the allylic chloride compound

Dry cuprous chloride is added to 3',4'-di(t-butyldimethylsiloxy) phenylacetylide magnesium bromide-containing reaction mixture which is then stirred for 15 minutes before the allylic chloride (step IV) (1.05 mol equiv.) dissolved in THF is added dropwise. The green suspension is refluxed for 45 minutes before an aqueous solution of ammonium chloride and KCN is added followed by ether extraction and work-up to yield the corresponding pent-4-ene-1-yn product. The product had the following values:

$\delta_H$(CDCl$_3$; 80 MHz, TMS): 0.23(12 H, s, —SiCH$_3$), 0.9(18 H, s, Si-CH$_3$), 3.35(2 H, d, J=5 Hz, H-2,3), 6.0(1 H, dt, J=5 Hz and J=16 Hz, H-4), 6.83(1 H, d, J=15 Hz, H-5) and 0.9–7.6(8 H, m, ArH).

X. Reaction of the allylic chloride compound with Lithium (3,4-di(t-butyldimethylsiloxyphenyl) acetylide A BuLi and dibromostyrene (1 mol equiv) reaction mixture, as prepared by procedure V containing cuprous chloride is stirred for 15 minutes before the allylic halide (1.1 mol eqv) dissolved in dry THF is added dropwise. The green suspension is refluxed for 45 minutes when an aqueous solution of ammonium chloride and KCN is added followed by extraction with ethyl acetate and work-up to yield the corresponding silyl ether pent-4-ene-1-yn product.

XI. Deprotection of the silyl ether product

To a solution of the silyl ether (1 eqv) in dry THF is added tetraethylammonium fluoride (4.8 eqv) in dry THF over a period of 15 minutes and the resulting mixture is stirred for an additional 3 hours at 23° C. The cooled reaction mixture is diluted with water and extracted several times with ethyl acetate. Solvent removal from dried MgSO$_4$ of the combined extracts under reduced pressure followed by residue purification by standard procedures provided rooperol.

$\delta_H$(CD$_3$OD; 80 MHz, TMS): 3.35 (2 H, d, J=5 Hz, H-2,3), 6.00(1 H, dt, J=5 Hz and J=16 Hz, H-4), 6.83(1 H, d, J=15 Hz, H-5) and 7.2-7.6(6H, m, ArH).

Similarly 1-phenyl-5-(3,4-dehydroxylphenylpent-4-en-1-yne-using equiv tetraethylammonium fluoride.

References

1. G. B. Marini-Bettolo, M Patamia, M Nicoletti, C Galeffi and I Messana: *Tetrahedron*, 1982, 38, 1683-1687.
2. S Drewes, A. J. Hall, R. A. Learmonth and U. J. Upfold: *Phytochemistry*, 1984, 23, 1313-1316.
3. E. J. Corey and P. L. Fuchs: *Tetrahedron Lett*, 1972, 3769-3772.
4. W. Koenigs and E. Knorr: *Ber.*, 1901, 34, 957-981.
5. H. Paulsen: *Angew.Chem.Int.Engl.Ed.*, 1982, 21, 155. *Angew.Chem.* 1982, 94, 184-201.
6. 
    (a) J. R. Pougny J. C. Jaquinet, M. Nassr, D. Duchet, M. L. Milat, and P. Sinay: *J.Am. Chem.Soc.*, 1977, 99, 6762-6763.
    (b) K. C. Nicolaou, S. A. Seitz, and D. P. Paphatjis: *J.Am.Chem.Soc.*, 1983, 105, 2430-2434.
7. S. Hasimoto, M. Hayashi and R. Noyori: *Tetrahedron Lett.*, 1984, 1379-1382.

We claim:

1. As a process for preparing a compound of the formula

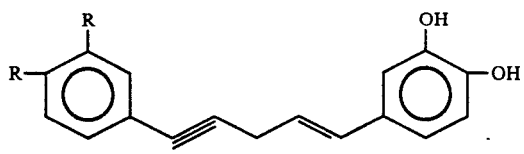

in which both Rs are H or —OH comprising the steps:

a. of treating the ethyl ester of caffeic acid with a trialkylsilyl chloride at ambient conditions in equimolar proportions in the presence of a base;

b. of reduction of the resulting product with an aluminium hydride reagent at sub-zero temperature and equimolar proportions to yield the corresponding allylic alcohol;

c. of halogenation of this allylic alcohol with thionyl chloride or a phosphorus trihalide to yield the corresponding allyl halide;

d. of coupling this allyl halide with the silyl ether of compound of the formula

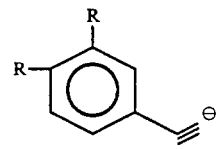

in refluxing ether solutions; and e. of hydrolysis of this coupled product with tetra alkyl ammonium flouride at ambient conditions and of equimolar proportions.

* * * * *